United States Patent [19]

Faraj

[11] Patent Number: 5,600,033
[45] Date of Patent: Feb. 4, 1997

[54] EPOXIDE ISOMERIZATION CATALYSTS

[75] Inventor: Mahmoud K. Faraj, Newtown Square, Pa.

[73] Assignee: ARCO Chemical Technology, L.P., Greenville, Del.

[21] Appl. No.: 461,086

[22] Filed: Jun. 5, 1995

Related U.S. Application Data

[62] Division of Ser. No. 324,033, Oct. 17, 1994, Pat. No. 5,455,215.

[51] Int. Cl.⁶ .............................. C07C 29/56; C07C 33/03
[52] U.S. Cl. ................................................ 568/908
[58] Field of Search ............................................ 568/908

[56] References Cited

U.S. PATENT DOCUMENTS

| | | | |
|---|---|---|---|
| 2,426,264 | 8/1947 | Fowler et al. | 568/908 |
| 2,986,585 | 5/1961 | Denton | 260/632 |
| 3,044,850 | 7/1962 | Denton | 23/107 |
| 3,274,121 | 9/1966 | Schneider | 252/437 |
| 3,285,967 | 11/1966 | Schaeffer | 260/614 |
| 3,789,078 | 1/1974 | Nolan et al. | 502/208 |
| 4,065,510 | 12/1977 | Schreyer et al. | 260/632 |
| 4,098,595 | 7/1978 | Lenz et al. | 65/17 |
| 4,243,422 | 1/1981 | Lenz et al. | 106/52 |
| 4,720,598 | 1/1988 | Sholte et al. | 568/908 |
| 5,262,371 | 11/1993 | Faraj | 502/78 |
| 5,292,974 | 3/1994 | Faraj | 568/908 |

FOREIGN PATENT DOCUMENTS

| | | | |
|---|---|---|---|
| 47-13009 | 4/1972 | Japan | 568/908 |
| 62-22736 | 1/1987 | Japan. | |
| 2036449 | 5/1993 | Spain. | |

*Primary Examiner*—Joseph Conrad
*Assistant Examiner*—Sreeni Padmanabhan
*Attorney, Agent, or Firm*—Jonathan L. Schuchardt

[57] ABSTRACT

Improved catalysts for isomerizing epoxides to allylic alcohols are disclosed. The catalysts contain lithium phosphate supported on high-purity silica. The use of high-purity silica as a support results in improved epoxide conversion and allylic alcohol selectivity, and reduced by-product generation. The invention includes a process for isomerizing epoxides using the catalysts. The process is well-suited to the manufacture of allyl alcohol from propylene oxide.

5 Claims, No Drawings

EPOXIDE ISOMERIZATION CATALYSTS

This is a division of application Ser. No. 08/324,033, filed Oct. 17, 1994, U.S. Pat. No. 5,455,215.

Field of the Invention

The invention relates to improved catalysts for isomerizing epoxides. In particular, the invention relates to silica-supported lithium phosphate catalysts, which are especially useful for vapor-phase isomerization processes.

BACKGROUND OF THE INVENTION

The discovery that epoxides (alkylene oxides) rearrange to give allylic alcohols in the presence of basic lithium phosphate catalysts sparked many efforts to improve catalyst lifetime, productivity, and selectivity. Allyl alcohol, the simplest allylic alcohol, is produced by isomerizing propylene oxide. Allyl alcohol is converted to useful allyl derivatives (diallyl phthalate, diallyl ether, diethylene glycol bis-(allyl carbonate), etc.) or is converted to 1,4-butanediol and its derivatives.

Two general isomerization processes are known: the vapor-phase isomerization process (see, for example, U.S. Pat. Nos. 3,044,850, 4,720,598, and 5,262,371), and the slurry-phase process (see, for example, U.S. Pat. No. 3,274,121). In the vapor-phase process, the epoxide is passed through supported or unsupported lithium phosphate at elevated temperatures, and the allylic alcohol is recovered and purified by distillation. A drawback of many vapor-phase processes: nonvolatile by-products accumulate on the catalyst surface over time and rapidly stifle catalyst activity.

The slurry-phase process, which is practiced commercially, was developed to overcome the catalyst deactivation problems of the vapor-phase process. In the slurry-phase process, lithium phosphate is suspended in a high-boiling oil. During the reaction, a portion of the catalyst suspension is continuously removed and centrifuged to separate the tar-containing oil from the catalyst. Tars are distilled from the oil, the lithium phosphate is washed with acetone, and the purified catalyst components are recycled to the reactor. Problems with the slurry-phase process include catalyst loss and high oil consumption.

A problem common to both the vapor-phase and slurry-phase processes is low selectivity to the allylic alcohols. Propylene oxide, for example, isomerizes to allyl alcohol, but also gives significant amounts of propionaldehyde, acetone, and 1-propanol.

Recently, we described (U.S. Pat. Nos. 5,262,371 and 5,292,974) improved epoxide catalysts for vapor-phase isomerization which comprise lithium phosphate and a neutral inorganic support, particularly alkali metal-exchanged zeolites. These catalysts give high allyl alcohol selectivities and good productivity in propylene oxide isomerizations. We indicated that silica can be used as a neutral inorganic support.

Gago et al. (Spanish Pat. No. 2,036,449) teach silica-supported lithium phosphate catalysts for isomerizing propylene oxide to allyl alcohol. The catalysts are prepared by reacting aqueous sodium phophate with an aqueous mixture of lithium and sodium hydroxides in the presence of silica that has a high surface area, followed by washing and drying of the resulting precipitated catalyst. The reference teaches that high-surface-area silicas are preferred, but says nothing more about the silica.

Our initial results with ordinary silica catalyst supports indicate that even high-surface-area silicas give low allylic alcohol selectivities in expoxide insomerizations.

When propylene oxide is isomerized, for example, the selectivity to allyl alcohol is somewhat low, and significant levels of by-products (propionaldehyde, acetone, 1-propanol) form.

Improved epoxide isomerization catalysts are needed, particularly those useful in a vapor-phase isomerization process. Preferred catalysts would give high selectivity to the allylic alcohols and a reduced proportion of non-selective by-products.

SUMMARY OF THE INVENTION

The invention is a supported catalyst useful for isomerizing epoxides. The catalyst comprises from about 5 to about 95 wt. % of lithium phosphate, and from about 5 to about 95 wt. % of a high-purity silica support. The silica support contains at least about 98 wt. % of silicon dioxide ($SiO_2$).

I surprisingly found that lithium phosphate supported on high-purity silica, i.e., silica that contains at least about 98 wt. % of silicon dioxide, gives improved epoxide conversions and allylic alcohol selectivities compared with lithium phosphate supported on ordinary silica, which typically has a silicon dioxide content of about 94 wt. %. The high-purity silica support contains reduced levels of trace impurities such as iron, zirconium, barium, calcium, and alumina. These impurities appear to encourage the formation of non-selective by-products in the epoxide isomerization process.

The invention includes a process for isomerizing epoxides to allylic alcohols. The process comprises heating an epoxide in the presence of a catalyst of the invention to produce an allylic alcohol. The process is well-suited to the isomerization of propylene oxide to produce allyl alcohol. The process gives relatively good selectivities to allyl alcohol while minimizing the formation of by-products, including propionaldehyde, acetone, and 1-propanol.

DETAILED DESCRIPTION OF THE INVENTION

The catalysts of the invention are useful for isomerizing epoxides to allylic alcohols. The catalysts comprise lithium phosphate and a high-purity silica support.

The lithium phosphate useful in the catalysts of the invention is commonly known as "basic lithium phosphate," and is preferably prepared in a strongly basic (pH >13) medium. Many methods are known in the art for preparing basic lithium phosphate; these methods will generally give a product that is suitable for use in the catalysts of the present invention. Suitable methods for preparing lithium phosphate are described, for example, in U.S. Pat. Nos. 3,044,850, 3,274,121, 4,720,598, and 5,262,371, the teachings of which are incorporated herein by reference.

Generally, an aqueous solution containing a soluble lithium salt (e.g., lithium hydroxide, lithium nitrate, lithium formate, or the like) is combined at any desired rate with an aqueous solution of phosphoric acid and/or one or more salts of phosphoric acid. The resulting precipitate of basic lithium phosphate is recovered by any convenient means such as filtration or centrifugation. Preferably, the lithium phosphate is washed with water to reduce its alkalinity, and is then dried.

One way to prepare suitable lithium phosphate for use in the invention is described in Example 1. Aqueous solutions of sodium phosphate and lithium/sodium hydroxide are simply combined, and the precipitate is filtered, washed, dried, and calcined. This lithium phosphate has a lithium/phosphorus ratio within the range of about 3.0 to about 3.4, excess hydroxide within the range of about 0 to about 0.40 moles per mole of lithium phosphate, and a surface area within the range of about 20 to about 50 m$^2$/g. Less than 3 wt. % of the particles have a particle size less than 4 microns.

Lithium phosphate is also commercially available from several suppliers, including Cyprus Foote Mineral, Rhone-Poulenc, Lithco, and others. These products are generally suitable for use in the catalysts of the invention.

The catalysts of the invention include a high-purity silica support. By "highpurity silica support," we mean silica that has a silicon dioxide ($SiO_2$) content of at least about 98 wt. %. Preferred silica supports will have a silicon dioxide content of at least about 99.5 wt. %. The silicon content of a silica sample is readily determined by elemental analysis.

Silica supports used in the invention will contain relatively low levels of impurities, including iron, zirconium, barium, calcium, alumina, and other trace elements. These impurities appear to encourage the formation of non-selective by-products when the support is used with lithium phosphate in an epoxide isomerization process. Thus, the amount of each impurity is preferably minimized. The silica support preferably contains less than about: 40 ppm of iron, 50 ppm of zirconium, 50 ppm of barium, 1000 ppm of calcium, 1 wt. % of alumina. Preferred silica supports contain less than about 0.1 wt. % of alumina as an impurity.

The silica supports used in the invention have relatively high surface areas (preferably greater than about 50 m$^2$/g, more preferably greater than about 100 m$^2$/g), although a high surface area alone is not sufficient to enhance the selectivity of the catalysts for making allylic alcohols. It is also important to use silica that has at least about 98 wt. % of silicon dioxide. See Example 5 and Comparative Example 8 below, in which both catalysts are prepared using silicas having high surface areas, but only the catalyst made with high-purity silica gives high selectivity to allyl alcohol in a propylene oxide isomerization process.

Silica supports useful in the invention are vitreous silicas. They are non-crystalline, synthetic products. Natural silicas, both crystalline and amorphous, do not have the requisite high $SiO_2$ content. The synthetic silicas useful in the invention are fused silicas (also called fumed silica, aerosils, pyrogenic silica). These are generally made by vapor-phase hydrolysis of silicon tetrahalides or silicon tetraalkoxides. Other methods for making fused silicas include vaporization of $SiO_2$, vaporization and oxidation of silicon, and high-temperature oxidation and hydrolysis of silicon compounds such as silicate esters.

The preparation of suitable high-purity silicas is described, for example, in U.S. Pat. Nos. 4,243,422 and 4,098,595, the teachings of which are incorporated herein by reference. The preparation of fused synthetic silica is described generally in *Kirk-Othmer's Encyclopedia of Chemical Technology* (1982), P. Danielson, "Vitreous Silica," Vol. 20, pp. 804–806. Suitable silicas for use in the supported catalysts of the invention are synthetic silicas that contain at least about 98 wt. % of silicon dioxide. Suitable high-purity silicas are available commercially from the PQ Corporation (for example, "HP-321" silica).

The relative amounts of lithium phosphate and silica support used in the catalysts of the invention is usually not critical. Generally, the catalysts will comprise from about 5 to about 95 wt. % of lithium phosphate and from about 5 to about 95 wt. % of the silica support. Preferred catalysts will comprise from about 25 to about 65 wt. % of lithium phosphate and from about 35 to about 75 wt. % of the silica support. Most preferred are catalysts comprising from about 35 to about 50 wt. % of the lithium phosphate and from about 50 to about 65 wt. % of the silica support. Catalysts that contain less than about 5 wt. % lithium phosphate are generally not sufficiently active, while using more than about 95 wt. % of lithium phosphate generally provides no additional benefit.

The supported catalysts of the invention are conveniently prepared by any suitable method for depositing the lithium phosphate on the high-purity silica support. In one method, high-purity silica and lithium phosphate are mixed in hot water, preferably for about 2 hours. The suspension is filtered, and the supported catalyst is washed with water, dried at elevated temperature (preferably at a temperature within the range of about 100° C. to about 200° C.), and is calcined (preferably at a temperature within the range of about 300° C. to about 350° C.). Example 2 illustrates this method of catalyst preparation.

If desired, solid lithium phosphate can simply be physically mixed with the silica support, but it is preferred to deposit the lithium phosphate on the surface of the support in an aqueous mixture.

The invention includes a process for isomerizing an epoxide to an allylic alcohol. The process comprises heating an epoxide in the presence of a supported catalyst of the invention to produce the allylic alcohol. The process may be a vapor-or slurry-phase process, although the catalyst is most suitable for a vapor-phase process.

Epoxides useful in the process of the invention are those capable of isomerizing to an allylic alcohol. These epoxides will have at least one hydrogen atom gamma to the epoxide oxygen. Examples of suitable epoxides include, but are not limited to, propylene oxide, 1,2-epoxybutane, 1,2-epoxypentane, 1,2-epoxyheptane, 1,2-epoxyoctane, isobutylene oxide, tetramethylethylene oxide, and the like, and mixtures thereof. Propylene oxide is preferred.

The process of the invention is performed at elevated temperatures, typically within the range of about 200° C. to about 350° C. A preferred range is from about 270° C. to about 320° C.; most preferred is the range from about 290° C. to about 310° C.

If desired, an inert gas may be used as a diluent for the epoxide in the process. For example, a mixed vapor stream of propylene oxide and nitrogen can be fed to the reaction zone. Suitable inert gases include nitrogen, argon, helium, and mixtures thereof.

The process of the invention can be performed at any suitable pressure, and is most conveniently performed at or slightly above atmospheric pressure.

The catalysts will normally deactivate slowly over time with continuous use, but their activity can be restored to normal activity by exposing the spent catalyst to air or pure nitrogen at temperatures within the range of about 300° C. to 400° C. for 6 to 24 h.

The following examples merely illustrate the invention. Those skilled in the art will recognize many variations that are within the spirit of the invention and scope of the claims.

EXAMPLE 1

PREPARATION OF BASIC LITHIUM PHOSPHATE

Sodium phosphate dodecahydrate (380 g) is dissolved in one liter of hot water (50°–60° C.). A solution prepared from sodium hydroxide (40 g), lithium hydroxide monohydrate (141.9 g), and one liter of hot water is rapidly combined with the sodium phosphate solution. The mixture is stirred for 1 h at 50°–60° C. The mixture is filtered, and the white precipitate of lithium phosphate is washed with hot water (4×800 mL) until the pH of the water wash is about 12. The lithium phosphate is dried under vacuum (120° C., 6 h) to give 106 g (91%) of basic lithium phosphate.

EXAMPLE 2

PREPARATION OF SILICA-SUPPORTED LITHIUM PHOSPHATE CATALYST (HIGH-PURITY SILICA)

A catalyst containing 37 wt. % lithium phosphate on high-purity silica is prepared as follows. Lithium phosphate (30 g) and high-purity silica (50 g, "HP-321" silica (99.6 wt. % $SiO_2$ by elemental analysis), product of PQ Corporation) are mixed in hot water (1000 mL) for 2 h. The mixture is filtered, and the solids are washed with water (3 ×300 mL). The solids are added under vacuum for 2 h at 120° C., and are calcined at 320°–350° C. for 12 h. The catalyst is pelletized and screened through 10–20 mesh screens before use. The same general procedure is used to prepare supported catalysts containing 25, 50, and 60 wt. % lithium phosphate.

COMPARATIVE EXAMPLE 3

PREPARATION OF SILICA-SUPPORTED LITHIUM PHOSPHATE CATALYST (ORDINARY SILICA)

The procedure of Example 2 is followed to prepare a catalyst containing 37 wt. % lithium phosphate, except that the silica support is a silica sample of ordinary purity, UCI silica, a product of United Catalysts, Inc., having an $SiO_2$ content of 94% by elemental analysis).

Properties of the high-purity silica and ordinary silica used as catalyst supports in these examples appear in Table 2.

EXAMPLES 4–7

VAPOR-PHASE ISOMERIZATION PROPYLENE OXIDE USING LITHIUM PHOSPHATE SUPPORTED ON HIGH-PURITY SILICA

Each of the catalysts prepared in Example 2 is used as a catalyst in a vapor-phase isomerization of propylene oxide as follows. Propylene oxide is slowly pumped into a vaporization zone (250° C. to 260° C.) using a liquid chromatography pump. The vaporized propylene oxide stream is combined with a stream of nitrogen, and the gaseous mixture is passed through a cylindrical column of the supported catalyst at 300° C. The feed rate of propylene oxide is adjusted to maintain a constant weight hourly space velocity (WHSV) value of about 2. The reaction products are condensed at −6° C. and are analyzed by gas chromatography. The results of the isomerization runs appear in Table 1.

COMPARATIVE EXAMPLE 8

VAPOR-PHASE INSOMERIZATION OF PROPYLENE OXIDE USING LITHIUM PHOSPHATE SUPPORTED ON ORDINARY SILICA

The procedure of Examples 4–7 is followed using the silica-supported lithium phosphate catalyst of Comparative Example 3 (ordinary silica). The results appear in Table 1.

As shown in Table 1, Example 5 and Comparative Example 8 (37 wt. % lithium phosphate catalysts), use of high-purity silica as a catalyst support results in higher conversions of propylene oxide, and higher allyl alcohol selectivities compared with the results obtained with lithium phosphate supported on ordinary silica. The proportion of non-selective by-products (propionaldehyde, acetone, and 1-propanol) is reduced by using a catalyst supported on high-purity silica.

As Table 2 indicates, the difference in selectivity is not related to a difference in surface area of the supports: the high-purity and ordinary silicas used have roughly the same surface areas (320–340 $m^2/g$). However, the content of other catalyst impurities (iron, zirconium, barium, calcium) differs, with the high-purity silica containing significantly less of these elements.

EXAMPLE 9

VAPOR-PHASE ISOMERIZATION OF ISOBUTYLENE OXIDE USING LITHIUM PHOSPHATE SUPPORTED ON HIGH-PURITY SILICA

The procedure of Examples 4–7 is followed, except that isobutylene oxide is used instead of propylene oxide in the isomerization procedure. The supported catalyst used contains 37 wt. % lithium phosphate. Conversion of isobutylene oxide is 95%; selectivity to methallyl alcohol is 96%.

TABLE 1

Propylene Oxide Isomerization to Allyl Alcohol using Lithium Phosphate on High-Purity Silica[1]

| Ex. # | $Li_3PO_4$ (wt. %) | PO conversion (%) | Product selectivities | | | |
|---|---|---|---|---|---|---|
| | | | Allyl alcohol | Propionaldehyde | Acetone | 1-Propanol |
| 4 | 25 | 39 | 92 | | | 0.5 |
| 5 | 37 | 42 | 93 | 4.4 | 1.8 | 0.4 |
| 6 | 50 | 68 | 94 | | | 0.45 |
| 7 | 60 | 80 | 93 | | | 0.45 |
| C8 | 37 | 34 | 88 | 6.8 | 2.9 | 0.65 |

[1]Examples 4–7 use high-purity silica (HP-321 silica, a product of PQ, 99.6 wt % $SiO_2$). Comparative Example 8 uses ordinary silica from United Catalysts, Inc., which has an $SiO_2$ content of 94.0 wt. %.

TABLE 2

Properties of Silica Supports

| Properties | High-Purity Silica (HP-321 silica) | Ordinary Silica (UCI silica) |
|---|---|---|
| Silicon (wt. %) | 46.0 | 44.0 |
| Silicon dioxide (wt. %) | 99.6 | 94.0 |
| Surface area ($m^2/g$) | 320 | 340 |
| Iron (ppm) | 38 | 490 |
| Zirconium (ppm) | 43 | 76 |
| Barium (ppm) | 32 | 110 |
| Calcium (ppm) | 890 | 2900 |

The preceding examples are meant only as illustrations. The following claims define the scope of the invention.

I claim:

1. A process for isomerizing an epoxide to an allylic alcohol, said process comprising heating an epoxide in the vapor phase in the presence of a supported catalyst which comprises:

(a) from about 5 to about 95 wt. % of lithium phosphate; and (b) from about 5 to about 95 wt. % of a silica support; wherein the silica support contains at least about 98 wt. % of silicon dioxide.

2. A process for isomerizing propylene oxide to allyl alcohol, said process comprising heating propylene oxide in the vapor phase at a temperature within the range of about 200° C. to about 350° C. in the presence of a supported catalyst which comprises:

(a) from about 25 to about 65 wt. % of lithium phosphate; and (b) from about 35 to about 75 wt. % of a silica support; wherein the silica support contains at least about 98 wt. % of silicon dioxide.

3. The process of claim 2 wherein the silica support contains at least about 99.5 wt. % of silicon dioxide.

4. The process of claim 2 wherein the selectivity to allyl alcohol (at 40% conversion of propylene oxide) is greater than about 90%.

5. A process for isomerizing an epoxide to an allylic alcohol, said process comprising heating the epoxide in the presence of a supported catalyst, wherein the supported catalyst comprises:

(a) from about 5 to about 95 wt. % of lithium phosphate; and (b) from about 5 to about 95 wt. % of a high-purity silica support;

wherein the silica support contains at least about 98 wt. % of silicon dioxide.

* * * * *